United States Patent
Mizutani et al.

(10) Patent No.: US 6,268,326 B1
(45) Date of Patent: Jul. 31, 2001

(54) BACTERICIDES AND CLEANING AGENTS FOR ERADICATING LEGIONELLA BACTERIA

(75) Inventors: Masumi Mizutani; Kazuyoshi Ichihara; Keiko Yamashita, all of Gifu (JP)

(73) Assignee: Showa Water Industries Co., Ltd. (JP)

(*) Notice: Subject to any disclaimer, the term of this patent is extended or adjusted under 35 U.S.C. 154(b) by 0 days.

(21) Appl. No.: 09/480,513

(22) Filed: Jan. 10, 2000

Related U.S. Application Data

(62) Division of application No. 09/256,136, filed on Feb. 24, 1999, now Pat. No. 6,172,029.

(30) Foreign Application Priority Data

Feb. 25, 1998 (JP) .................................................. 10-043929

(51) Int. Cl.$^7$ ...................................................... C11D 1/75
(52) U.S. Cl. ........................................................... 510/383
(58) Field of Search ..................................... 510/382, 383

(56) References Cited

U.S. PATENT DOCUMENTS

| 3,296,145 | 1/1967 | Findlan et al. ................. 252/106 |
| 3,410,903 | 11/1968 | Solomon ......................... 260/583 |
| 3,484,523 | 12/1969 | Findlan et al. ................. 424/248 |
| 3,835,057 | 9/1974 | Cheng et al. ................... 252/107 |
| 4,606,850 | 8/1986 | Malik ............................... 252/528 |
| 4,961,878 | * 10/1990 | Mullins ........................ 252/389.3 |
| 5,342,578 | * 8/1994 | Agrawal et al. .................. 422/13 |
| 5,516,459 | 5/1996 | Van Eenam .................... 252/547 |
| 5,556,833 | 9/1996 | Howe ............................... 510/189 |
| 5,656,582 | 8/1997 | Kuchikata et al. ............ 504/206 |
| 5,827,810 | 10/1998 | Brodbeck et al. ............. 510/369 |
| 5,858,117 | 1/1999 | Oakes et al. ..................... 134/27 |

FOREIGN PATENT DOCUMENTS

| 2708278 | * 2/1995 | (FR) . |
| 1514490 | 6/1978 | (GB) . |
| 2178960 | 2/1987 | (GB) . |
| 2274393 | 1/1993 | (GB) . |
| 5-112427 | 5/1993 | (JP) . |
| 8157899 | 6/1996 | (JP) . |

* cited by examiner

Primary Examiner—John Hardee
(74) Attorney, Agent, or Firm—Madson & Metcalf

(57) ABSTRACT

An antimicrobial agent suitable for eradicating Legionella contains at least one amine oxide represented by the formula (1) and/or at least one amine oxide represented by the formula (2).

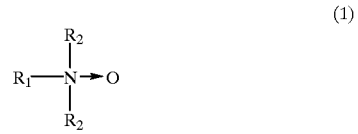

(1)

$R_1$ represents $C_nH_{2n+1}(OC_2H_4)_m$, n varies from 12 to 18, m varies from 0 to 10, $R_2$ represents a hydrogen or alkyl group having from 1 to 4 carbon atom(s), and the solid arrow represents a coordinate bond between a nitrogen and oxygen.

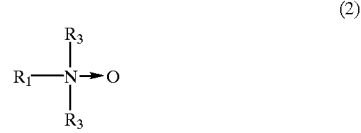

(2)

$R_1$ represents $C_nH_{2n+1}(OC_2H_4)_m$, n varies from 12 to 18, m varies from 0 to 10, $R_3$ represents $(C_pH_{2p})OH$ with p varying from 1 to 4, and the solid arrow represents a coordinate bond between a nitrogen and oxygen.

23 Claims, No Drawings

BACTERICIDES AND CLEANING AGENTS FOR ERADICATING LEGIONELLA BACTERIA

This application is a divisional of application Ser. No. 09/256,136, filed Feb. 24, 1999 now U.S. Pat. No. 6,172,029.

BACKGROUND OF THE INVENTION

The present invention relates to bactericides, and more particularly, to bactericides that kill harmful microorganisms including those belonging to the genus Legionella.

Heat exchangers used in air-regulators, or the like, are generally provided with fins to exchange heat. The fins of a typical heat exchanger are exposed to ambient air to release heat into the air. A stream of air may be forced through the fins to facilitate the heat exchange between the fins and the air. Accordingly, the fins are subjected to moisture and dust particles present in the air. This provides a suitable environment for the growth of health-impairing microorganisms such as fungi or pathogenic bacteria including the genus Legionella.

Certain acidic or basic solutions, known as pH regulators, surfactants, organic solvents, or mixtures thereof have been used as cleansing agents for equipment, including heat exchanging fins, where microorganisms are likely to grow. Japanese Unexamined Publication No.8-157899 describes a spray-type cleaning agent for spraying washing agent foam onto surfaces of equipment to be cleansed. The foamed agent stays on the surface of the parts, e.g. fins, for an extended period of time.

Although it can effectively remove such deposits as scale or sediment, this cleaning agent is not capable of completely killing or removing microorganisms that grow on the surface of the fins. The use of the agent in a large amount can suppress the growth of microorganisms to some extent. Complete sanitization, however, can not be achieved with the agent due to its nature as a cleaner rather than a bactericide. Because of the agent's lack of bactericidal effect, microorganisms that have not been removed can readily proliferate. This may lead to clogging of the drainage pipe by plaque formed by bacteria, and subsequently, to an incomplete discharge of collected condensation water, which collects in a discharge pan.

Conventional sanitizing chemicals include strong oxidizing reagents such as hydrogen peroxide, sodium hypochlorite and calcium hypochlorite, as well as bactericides including glutaraldehyde, and strong acids including hydrochloric acid. Twenty-four hour hot tubs, which are often used in Japan, recirculate the same water repeatedly while the water is sanitized and purified with an integrated biological purification system. When applied to the bath system, the above-mentioned chemicals work non-selectively on a wide range of microorganisms, killing not only harmful bacteria such as Legionella but also favorable bacteria inhabiting the system. Consequently, the purifying effect of the system would be lost.

In addition, gas is produced when hydrogen peroxide and sodium hypochlorite are used in bactericidal application. The gas can cause a problem in the purification system in that the discharge chamber of the pump fills with the gas, and consequently the pump loses its prime. As a result, the water flow in the piping system is disrupted.

Sodium hypochlorite and calcium hypochlorite are highly corrosive to metal. Also, they may produce toxic gas when mixed with other reagents. These factors substantially restrict application of the reagents.

Strong acids such as hydrochloric acid are not suitable used for sanitizing purposes unless an anti-corrosive coating is applied to protect metal parts. Sanitization with strong acids, therefore, requires by certain restriction.

SUMMARY OF THE INVENTION

Considering the above-mentioned problems associated with the prior art, the objective of the present invention is to provide antimicrobial agents with fewer restrictions upon application.

To achieve above objective, the present invention provides an antimicrobial agent containing at least one amine oxide represented by the formula (1), and/or at least one amine oxide represented by the formula (2):

(1)

wherein $R_1$ represents $C_nH_{2n+1}(OC_2H_4)_m$, n varies from 12 to 18, m varies from 0 to 10, $R_2$ represents a hydrogen or alkyl group having from 1 to 4 carbon atom(s), and the solid arrow represents a coordinate bond between a nitrogen and oxygen.

(2)

wherein $R_1$ represents $C_nH_{2n+1}(OC_2H_4)$m, n varies from 12 to 18, m varies from 0 to 10, $R_3$ represents $(C_pH_{2p})OH$ with p varying from 1 to 4, and the solid arrow represents a coordinate bond between a nitrogen and oxygen.

Other aspects and advantages of the present invention will become apparent from the following description.

DETAILED DESCRIPTION OF THE PREFERRED EMBODIMENTS

All of the bacterial species belonging to genus Legionella are incapable of metabolizing carbohydrates such as glucose. Instead, they use amino acids as a source of carbon and energy. For this reason, Legionella grow in the amino acid rich environment of the cells of heterotrophic protozoa, such as amoeba, that feed on bacteria.

Though the life cycle of Legionella is not understood very well, it is thought to be largely dependent upon that of the host protozoan, as Legionella are considered to be asporogenous(not forming spores). Therefore, eradicating the prospective host protozoa is as important a step as is eradicating the bacteria that are free from their hosts, in an effort to completely prevent infection.

Characteristics of antimicrobial agents comprising the bactericides of the present invention are described in the following.

The bactericides of the present invention contain at least one amine oxide, which is shown by chemical formula (1) or (2):

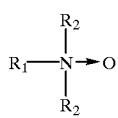

(1)

wherein $R_1$ represents $C_nH_{2n+1}(OC_2H_4)_m$, n varies from 12 to 18, m varies from 0 to 10, R2 represents a hydrogen or an alkyl group with carbon atom(s) varying from 1 to 4, and the solid arrow represents a coordinate bond between a nitrogen and an oxygen;

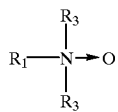

(2)

wherein $R_1$ represents $C_nH_{2n+1}(OC_2H_4)_m$, n varies from 12 to 18, m varies from 0 to 10, $R_3$ represents $(C_pH_{2p})OH$ with p varying from 1 to 4, and the solid arrow represents a coordinate bond between a nitrogen and an oxygen. More favorably, the amine oxide shown in the formula (1) or (2) has a value for n that varies from 12 to 14 and a value for m that varies from 0 to 5. If n is an integer smaller than or equal to 11 in the formula (1) or (2), then the amine oxide can become unstable. Conversely, if n is an integer greater than or equal to 19, then the amine oxide can become highly hydrophobic and insoluble in water.

The amine oxide compounds of the present invention include dimethyl lauryl amine oxide and dihydroxymethyl lauryl amine oxide. These amine oxides have anti-microbial activity over a wide range of pH. In addition, these compounds are highly effective degreasing agents and foam produced during the course of degreasing is long-lasting. Because of these characteristics, the amine oxides are suitably used in cooling towers or whirlpool baths as a sanitizing agent.

Since most conventional bactericides have little solubility in water, organic solvents are required in preparing liquid bactericides to dissolve the active ingredients. In contrast, the amine oxide compounds described above are readily soluble in water and are good surfactants due to the fact that the compound molecule contains both a hydrophilic portion, i.e., a polar coordinate bond between a nitrogen atom and an oxygen atom, and a hydrophobic group, i.e., $R_1$ group. How each of the amine oxides can kill Legionella as well as their host protozoa has not yet been fully understood, but it is believed that the hydrophobic group in the amine oxide increases the affinity of the compound molecule to the surface of bacterial cells as well as to that of protozoan cells, and thereby contributes to high anti-microbial activity of the compound.

It is preferred that each of the amine oxides described above is prepared as an aqueous solution to facilitate sanitization. It is desirable that the sanitization of Legionella and host protozoa thereof be conducted within three hours. With regard to this, the molarity of the solution of the amine oxide is preferably in the range of from 0.096 to 50 mM. Sufficient anti-microbial effect will not be achieved with molar concentrations of less than 0.096 mM. Though effective, it is economically unfavorable when the molar concentration of the solution is greater than 50 mM.

Twenty-four hour tubs and sanitization thereof will now be described. A twenty-four hour tub uses utilizes a biological purification system to purify the water in the tub so that the same water can be used continuously. A twenty-four hour tub has a water inlet and an outlet, which are placed such that they are submerged when water fills the tub. A pump, a heater, and a purification tank are arranged between the inlet and the outlet, and they are connected by piping for the circulation of water. The water is purified as it flows through the system. Contamination in the water are removed at the purification tank and are degraded by microorganisms inhabiting the tank. Since killing of the useful bacteria in the purification system will lead to the loss of purifying ability, selective anti-microbial activity is required for the bactericides used to eliminate Legionella in the system.

Each of the amine oxides described above is suitable for eradicating Legionella in biological purification systems such as that of twenty-four hour tubs, since Legionella and host protozoa are selectively eliminated from the system, while killing of useful bacteria is avoided.

The effect of the amine oxide compounds mentioned above will now be described. The amine oxides described above each can kill Legionella and/or host protozoa thereof selectively.

The amine oxides described in each of the embodiments are water-soluble. Therefore, the use of organic solvents harmful to useful microorganisms can be dispensed with, and damage to useful microorganisms is avoided. Accordingly, continuous operation of the biological purification system is possible.

In addition, each of the amine oxide compounds of the present invention is applicable in a broad range of pH. This broadens application of the compounds to a variety of places ranging from equipment such as air-conditioning cooling towers or twenty-four hour tubs to hand wash soap.

Furthermore, the amine oxides of the present invention are economically advantageous since sufficient antimicrobial effects can be achieved at molarities from 0.096 to 50 mM.

Also, during sanitization, the amine oxides of the present invention will not produce gas that can disrupt the pump operation.

Finally, the amine oxide compounds of the present invention are not corrosive to metal.

FIRST EMBODIMENT

Shown below are explanatory experiments and controls thereof to show the bactericidal effect of the bactericides on Legionella. Testing methods of the experiments are based on "*Testing methods for the effect of water sanitizing agents*" in *Guideline for prevention of Legionellosis,* published by the Building Management Education Center, and edited by the Planning Division of the Environmental Health Bureau of the Ministry of Health and Welfare of Japan.

Experiment 1

In this experiment, UNISAFE A-LM is used as an amine oxide. UNISAFE A-LM is a dimethyl lauryl amine oxide available from NIHON YUSHI Co., Ltd., Tokyo, Japan, and has a structure where n is 12, m is 0, and $R_2$ is a methyl in formula (1).

First, an *L. pneumophila* strain was incubated on a BCYEα agarose medium at 37 degrees Celsius for three days. A suspension of *L. pneumophila* was prepared by suspending a mass of incubated bacteria in distilled water. Turbidity of the suspension was adjusted to 1 on the MacFarland scale. The turbidity of 1 on the MacFarland scale corresponds to a number of cells of about $10^8$ CFU/ml in the suspension. Aqueous amine oxide solutions of different molar concentrations were prepared as shown in table 1, using UNISAFE A-LM. The bacteria suspension was diluted by a factor of 100 with the amine oxide solution. Portions of the mixture were incubated at 30 degrees Celsius for 15, 60, and 180 minutes. After the incubation period, the mixtures were inoculated onto separate plates containing BCYEα medium and incubated for three days at 37 degrees Celsius. Antimicrobial effect was determined based on the presence of colonies formed in each culture after three days.

Table 1 shows the result of the tests for the bactericidal effect. The circles indicate absence of the colonies, which implies that the agent had a significant effect. The crosses indicate presence of the colonies, suggesting that the agent did not have sufficient bactericidal effect.

Experiment 2

In this experiment, UNISAFE A-LY was used as an amine oxide. UNISAFE A-LY is a trioxyethylene dimethyl lauryl amine oxide, manufactured by NIHON YUSHI Co., Ltd. The compound has a structure in which n is 12, m is 3, and $R_2$ is a methyl in the preceding formula (1). Solutions of the compound having different molar concentrations were prepared as shown in table 1. Using the solutions, the same procedures were followed as in the experiment 1. The results are shown in table 1.

Experiment 3

In this experiment, UNISAFE A-LE was used as an amine oxide. UNISAFE A-LE is a dihydroxy ethyl lauryl amine oxide manufactured by NIHON YUSHI Co., Ltd. It has a structure in which n is 12, m is 0, and $R_3$ is a hydroxy ethyl in formula (2). Solutions of the amine oxide with different molar concentrations were prepared as shown in table 1. Same procedures were followed using the solutions as in the experiment 1. The results are shown in table 1.

TABLE 1

| Contact Time (min) | Experiment 1 Concentration(M) | Effect | Experiment 2 Concentration(M) | Effect | Experiment 3 Concentration(M) | Effect |
|---|---|---|---|---|---|---|
| 15 | $3.1 \times 10^{-5}$ | x | $1.9 \times 10^{-5}$ | x | $2.4 \times 10^{-5}$ | x |
| 60 | | x | | x | | x |
| 180 | | x | | x | | x |
| 15 | | | $9.6 \times 10^{-5}$ | x | | |
| 60 | | | | o | | |
| 180 | | | | o | | |
| 15 | $3.1 \times 10^{-4}$ | x | $1.9 \times 10^{-4}$ | x | $2.4 \times 10^{-4}$ | x |
| 60 | | o | | o | | x |
| 180 | | o | | o | | o |
| 15 | $4.6 \times 10^{-4}$ | o | $2.1 \times 10^{-4}$ | o | $4.2 \times 10^{-4}$ | o |
| 60 | | o | | o | | o |
| 180 | | o | | o | | o |
| 15 | $3.1 \times 10^{-3}$ | o | $1.9 \times 10^{-3}$ | o | $2.4 \times 10^{-3}$ | o |
| 60 | | o | | o | | o |
| 180 | | o | | o | | o |
| 15 | $3.1 \times 10^{-2}$ | o | $1.9 \times 10^{-2}$ | o | $2.4 \times 10^{-2}$ | o |
| 60 | | o | | o | | o |
| 180 | | o | | o | | o |

The result indicates that all of the Legionella were killed in three hours at amine oxide concentrations greater than or equal to 0.096 mM.

Experiments 4, 5, and 6

The anti-bacterial effects of amine oxides on bacteria other than Legionella were examined. In each of the experiments 4, 5, and 6, UNISAFE A-LM was used as an amine oxide. The compound was dissolved in distilled water to prepare aqueous solutions having different molar concentrations of the compound as shown in table 2. The pH of each solution was measured. Suspensions of soil bacteria were prepared by suspending soil in distilled water. The soil suspensions were diluted by a factor of 10 with the UNISAFE solutions. The diluted solutions were incubated for 15 minutes at 30 degrees Celsius. After the incubation period, the solutions were inoculated onto plates containing growth media. The plates were then incubated for 24 hours at 37 degrees Celsius. The number of bacteria per unit volume of the original solution (CFU/ml) was calculated by counting the number of colonies formed on each plate after 24 hours. The results are shown in table 2.

Control 1

The same procedures were followed as in Experiments 4, 5, and 6 except that distilled water was used instead of bactericide solutions. The results are shown in table 2.

TABLE 2

| | Control 1 | Exp. 4 | Exp. 5 | Exp. 6 |
|---|---|---|---|---|
| Concentration of A-LM(M) | 0 | $3.1 \times 10^{-4}$ | $3.1 \times 10^{-3}$ | $3.1 \times 10^{-2}$ |
| pH | 7.0 | 6.1 | 6.7 | 7.6 |
| CFU/ml | $1.5 \times 10^5$ | $5.0 \times 10^4$ | $3.0 \times 10^4$ | $3.0 \times 10^4$ |

The figures for experiment 5 in table 2 indicate that about 20 percent of the soil bacteria survived in the UNISAFE A-LM solution with molar concentration of 3.1 mM. Given that almost 100 percent of Legionella were killed using a bactericide concentration of 3.1 mM, it is apparent that the bactericides selectively kill Legionella. As can be seen from the result of experiment 6, about 20 percent of the soil bacteria thrived in the amine oxide solutions of 31 mM, which is 10 times as high as the concentration at which no Legionella survived. The measurement of the pH values of the solutions used in each experiment shows that the antibacterial effect of the amine oxide compounds was independent of the pH of the solutions.

SECOND EMBODIMENT

Alternatively, the amine oxides used in experiment 1 may be used in conjunction with other water-soluble bactericides such as thiazoles, chlorophenols, or quaternary ammonium salts. The mixture has a broader spectrum due to the universal effects of the bactericides added. The mixed bactericides are preferred, especially when eradication of the entire population of microorganisms in the environment is desired, as in the case of cooling towers.

THIRD EMBODIMENT

The amine oxides according to the present invention may be used in combination with detergents containing such surfactants as sodium nonyldiphenylethersulfonate and common soap. The mixed agent is capable not only of selectively killing Legionella but also of removing deposits, e.g., scale and sediment, formed inside hot water pipes. The agents are, therefore, suitable for a biological purification system.

FOURTH EMBODIMENT

The amine oxides according to the present invention can be used in place of common surfactants contained in conventional cleansing agents. A significant cleaning effect, as well as a selective bactericidal effect, is obtained when the agents are used in a biological purification system.

FIFTH EMBODIMENT

The amine oxides according to the present invention may be used in conjunction with washing agents that are applied on the human body or to kitchen appliances that contact the human body, examples being hand-washing soap and dish-washing detergent. Cleaning and sanitizing effects are achieved also in this case. The use of the agents in this manner contributes to hygiene since the transmitting route of Legionella is terminated.

SIXTH EMOLUMENT

In this embodiment, the cleaning agent is prepared as a mixture of a bactericide(s) and a washing agent(s). The bactericide contained in the cleaning mixture is an amine oxide either of the chemical formulae (1) and (2). The cleaning agent is contained in a spray can along with compressed gaseous nitrogen. When in use, foam of the cleaner is sprayed out from the spray can, and the foam adheres the surface to be cleaned and/or sanitized. The cleaning agent normally contains a pH regulator and a surfactant as washing agents. There is also contained another agent (thickener) to increase the viscosity of the cleaner to a desired degree, so that it remains on the surfaces to which it is applied for a longer time.

A problem with conventional spray-type agents is that they fail to penetrate narrow spaces like those between fins due to the fact that the agent foams immediately after it is sprayed out. In order to solve this problem, the cleaning agent of the present invention contains a foaming agent that produces foam after a certain period of time after being sprayed out. A second water-soluble bactericide to kill microorganisms, in addition to Legionella, is also included.

In this embodiment, an amine oxide represented by either one of the preceding chemical formulae (1) and (2) is used as a bactericidal agent. The cleaner preferably contains from 0.007 to 7% by weight of the amine oxide. 0.007% of amine oxide by weight corresponds to 0.31 mM of UNISAFE A-LM, 0.19 mM of UNISAFE A-LY, or 0.24 mM of UNISAFE A-LE. An amine oxide content less than 0.007% by weight significantly deteriorates work efficiency, since it takes longer to complete sanitization (more than an hour). An amine oxide content greater than 7% becomes costly. Therefore, an amine oxide content from 0.07 to 2% is more preferable.

An acidic or basic compound is used as a pH regulator. Preferred basic compounds include sodium hydroxide, potassium hydroxide, phosphates, and silicates, since most microorganisms can not survive in a strongly basic environment. Sodium metasilicate is preferably used in a heat exchanger since fins in heat exchangers are typically made of aluminum. Sodium metasilicate makes aluminum surface hydrophilic. Therefore, moisture in the air tends to condense on the aluminum surface when the surface is treated with sodium metasilicate. The water that condenses on the surface of the fins takes heat away therefrom when it evaporates, increasing the heat transfer efficiency of the fins. The pH regulator content in the cleaner is preferably in the range of from 0.1 to 15% by weight. Though effective, it is economically unfavorable when the pH conditioner exceeds 15% by weight.

Organic solvents may be added to the cleaning agent to effectively remove organic scale or sediment. These solvents include alcohols and esters that can facilitate the sanitizing effect of the cleaner. The types and amounts of the solvents to be added is not limited. However, ethanol is preferred alcohol because of its high sanitizing effect. Methyldiethanolamine is preferred as an amino alcohol agent. An effective methyldiethanolamine content is 20% by weight. Addition of amino alcohols to the cleaner is optional since amino alcohols yield unpleasant odors. Amino alcohols can also serve as a pH regulator since they exhibit bacisity when diluted with water.

Surfactants are added for cleansing and sanitizing purposes. A surfactant is selected from the group consisting of cationic, anioinic, and non-ionic surfactants. Sodium dodecyl sulfate(SDS), an anionic surfactant, is preferred since the compound has a strong bactericidal effect as well as a good cleansing ability. SDS can denature proteins and destroy bacterial cell walls, thereby producing a strong anti-microbial effect. The content of SDS in the cleaning agent is preferably from 0.01 to 15% by weight. The cleaner is inadequate at concentrations less than 0.01% by weight. Though effective, the cleaner becomes costly at the concentrations greater than 15% by weight.

The following compounds may be used as a thickener: sodium alginate, propylene glycol alginate esters, carboxymethyl cellulose(CMC) esters, sodium carboxy methyl cellulose, starch sodium glycolate, starch sodium phosphate esters, methyl cellulose, sodium polyacrylate, cellulose esters, alginic acid, casein, and poly-N-vinyl acetamide.

Chemical properties of a thickener should not be affected by other ingredients present in the cleaning agent. In this regard, cellulose esters are preferably used, especially in basic solutions. When cellulose esters are present in the cleaner, propylene glycol may be added to dissolve the cellulose esters in the solution.

The viscosity of the cleaning mixture is preferably adjusted to a value of from 5 to 1,000 cP. The resulting foam will become less sticky and will easily flow off the surface when the viscosity is less than 5 cP. In contrast, with viscosities greater than 1,000 cP, the cleaner can not be propelled by aerosol from a spray can, and fails to effectively enter narrow spaces between aluminum fins. More preferably, the viscosity of the cleaning mixture is adjusted to a value from 5 to 300 cP.

Compounds, such as iso-pentane and n-pentane, the boiling points of which lie in the room temperature range from 10 to 40 degrees Celsius, are preferably used as a foaming agent. Sufficient foaming will be obtained if the amount of foaming agent is greater than 5% by weight of the cleaner.

Water-soluble bactericides such as thiazoles, chlorophenols, or quaternary ammonium salts may be used as a second bactericidal agent. Benzoisothiazolone is preferable as a thiazole. 2,2'-methylenebis(4-chlorophenol) is preferable as a chlorophenol bactericide. Benzalkonium chloride is preferable as a quaternary ammonium salt. The content of the bactericidal agent in the cleaning mixture is preferably in the range of from 0.001 to 10% by weight. If the bactericide forms less than 0.001% by weight of the mixture, the bactericidal effect is insufficient. Conversely, if the amount of the bactericide is greater than 10% by weight, while the bactericidal effect is sufficient, production costs are unnecessarily high. The amount of bactericidal agent that is sufficient for killing bacteria is in the range of from 0.02 to 1% of the mixture by weight. The amount of bactericidal agent that is sufficient for killing mold is in the range of 0.1 to 1% by weight.

Experiments described below were conducted to help understanding of sixth embodiment of the present invention.

Experiment 7

In this experiment, the cleaning mixture contained 0.7% by weight of UNISAFE A-LM (31 mM), as an amine oxide, 1.5% by weight of sodium metasilicate, as a pH regulator, 20% by weight of N-methyldiethanolamine, as a solvent and a pH regulator, 4.2% by weight of polyoxyethylene oleyl ether, and 2.0% by weight of sodium dodecyl sulfate, as a surfactant. Cellulose ester was added as a thickener and the viscosity of the mixture was adjusted to 6 cP. 10% by weight of propylene glycol was added to dissolve the cellulose ester. 5% by weight of iso-pentane was also added as a foaming agent. Compressed gaseous nitrogen was used as propellant. Table 3 shows some of important properties of the cleaning mixture.

The following measurements were taken:

Aerosol Traveling Distance

The cleaning mixture was sprayed from in front of aluminum fins that had a depth of 7 cm. The numbers indicate how far an aerosol of the cleaning mixture traveled in the air into spaces between the fins (in centimeter), that is, the greater the number, the further the aerosol traveled.

Foam Descending Time

The cleaner was sprayed onto a surface of an upright metal plate for a certain period of time. The time the resulting foam took to travel down 10 cm on the surface was measured. The greater the measurement, the longer the foam stayed where it was applied.

Foam Falling Time

The cleaner was sprayed onto the lower end of an aluminum fin. The time the resulting foam took before it dripped from the fin was measured. The greater the measurement, the longer the foam stayed where it was applied.

Foam Diminishing Time

The cleaner was sprayed into a 100 ml glass beaker until the beaker was filled up to the top. The time during which the foam diminished was measured. The foam was considered to be diminished when the surface of the solution appeared. The greater the time, the more stable the foam.

Detergency

Artificial scale manufactured according to Japan Industrial Standard NO.K-3362 was sprayed onto fins, and the fins were left for one week. After one week, the fins were sprayed with the cleaner, and the foam was rinsed out after 15 minutes. The cleansing effect, or detergency, was determined based on how much of the scale was removed.

Anti-Legionella Activity

The anti-Legionella activity of the cleaning agent of the embodiment was determined in the same manner as that in the preceding experiments 1,2,and 3.

General Anti-bacterial Activity

The bactericidal activity of the cleaner was determined in the same manner as that in the preceding experiments 4,5, and 6.

In the following tables, a circle indicates that the particular mixture exhibited the desired effect (100 to 90%) with respect to detergency, anti-Legionella activity, or anti-bacterial activity, which were evaluated as described above. A square indicates that the mixture showed satisfactory effectiveness (90 to 50%) though less effective than those marked with circles. A triangle indicate that the cleaner was somewhat effective (50 to 10%) but less so than those marked with squares. A cross indicates that the mixture showed little or no effectiveness.

Experiments 8, and 9

In these experiments, the viscosity of the cleaner was increased by increasing the cellulose ester content in the mixture. The viscosity for experiment 8 was adjusted to the value of 12, and to the value of 292 for experiment 9. The compositions of the mixtures are shown in table 3. The same properties were evaluated as were evaluated in the experiment 7. The results are shown in table 3.

Experiments 10, 11, 12, 13, and 14

In these experiments, the mixtures for experiments 10,11, and 12 were free of sodium metasilicate. The mixtures for experiments 13 and 14 were prepared without sodium metasilicate and amino alcohol. Therefore, the pH values of the mixtures were lower than those in experiments 8 and 9. The compositions of the mixtures are shown in table 4.

Experiment 15

The composition for experiment 15 was the same as that for experiment 14, except that sodium metasilicate was added to the mixture. The composition of the mixture is as shown in table 4.

Experiments 16, 17, and 18

In these experiments, benzoisothiazolone and benzalkonium chloride were added as a second bactericide, in addition to amine oxide, sodium metasilicate, and surfactants, to further the anti-bacterial effect. The compositions of the mixtures are as shown in table 5.

Experiments 19, 20, 21, and 22

The compositions of the mixtures for these experiments are as shown in table 6. The amount of metasilicate and the amount of a second bactericide were changed in these experiments.

Experiments 23, 24, 25, and 26

The compositions of the mixtures for these experiments are as shown in table 6. The surfactant amounts were changed in these experiments.

In Experiments 10 to 26, the same properties that were evaluated in experiment 7 were evaluated. The results are shown in tables 3, 4, 5, and 6.

Control 2

In this control experiment, a mixture was prepared without the foaming agent (iso-pentane) and without the thickener(cellulose ester). The other ingredients were mixed with using same ratio as used in experiment 7. The composition is as shown in table 7. The effects of the foaming agent and the thickener can be determined by comparing the result of Control 2 with experiment 7. LPG was used as a propellant.

Control 3

The mixture serves as a control for experiment 7. The mixture had the same composition as that used in experiment 7 except that it was free of foaming agent (iso-pentane). The composition of the mixture is as shown in table 7. The effects of the foaming agent and the thickener can be determined by comparing the results of Control 2 with those of experiment 7. LPG was used as a propellant. In Control 3, the mixture was evaluated with regard to the same properties as in experiment 7.

Control 4

The mixture serves as a control for experiment 7. The mixture had the same composition as that for experiment 7 except that amine oxide and the foaming agent were not added to the mixture. The composition of the mixture is as shown in table 7. LPG was used as a propellant.

Control 5

The mixture for control 5, which served as a control experiment of experiment 8, contained neither amine oxide nor foaming agent. Otherwise, the composition of the control mixture was the same as that of experiment 7. The composition of the mixture is as shown in table 7. LPG was used as a propellant.

Control 6

The mixture for control 6, which served as a control experiment for experiment 15, was free of surfactants. Otherwise, the composition of the control mixture was the same as that of experiment 15. The composition of the mixture is as shown in table 7. Gaseous nitrogen was used as the propellant.

Control 7

The mixture for control 7, which served as a control experiment for experiment 8, contained neither amine oxide nor sodium metasilicate. Otherwise, the control mixture had the same composition as that of experiment 8. The composition of the mixture is as shown in table 7. Gaseous nitrogen was used as the propellant. The same properties as those in experiment 7 were evaluated. The results are shown in table 7.

TABLE 3

| ingredients | Exp. 7 | Exp. 8 | Exp. 9 |
|---|---|---|---|
| amine oxide | 0.7 | 0.7 | 0.7 |
| sodium metasilicate | 1.5 | 1.5 | 1.5 |
| aminoalcohol | 20 | 20 | 20 |
| nonion surfactant | 4.2 | 4.2 | 4.2 |
| anion surfactant | 2 | 2 | 2 |
| benzo-isothiazolone | 0 | 0 | 0 |
| 2,2'-MBCP | 0 | 0 | 0 |
| cellulose ester | 0.1 | 0.3 | 0.5 |
| propyleneglycol | 10 | 10 | 10 |
| isopentane | 5 | 5 | 5 |
| water | 56.5 | 56.3 | 56.1 |
| viscosity(cP) | 6 | 12 | 292 |
| Aerosol traveling distance (cm) | 7 | 7 | 5 |
| Foam descending time (s/cm) | 6.3 | 71.7 | 276 |
| Foam falling time(s) | 730 | 940 | 3600 |
| Foam diminishing time(s) | 4200 | 7800 | 9780 |
| Detergency | ○ | ○ | ○ |
| Anti-Legionella activity | ○ | ○ | ○ |
| General anti-bacterial activity | □ | □ | □ |

TABLE 4

| ingredients | Exp. 10 | Exp. 11 | Exp. 12 | Exp. 13 | Exp. 14 | Exp. 15 |
|---|---|---|---|---|---|---|
| amine oxide | 0.7 | 0.7 | 0.7 | 0.7 | 0.7 | 0.7 |
| sodium metasilicate | 0 | 0 | 0 | 0 | 0 | 1.5 |
| aminoalcohol | 20 | 20 | 20 | 0 | 0 | 0 |
| nonion surfactant | 4.2 | 4.2 | 4.2 | 2 | 2 | 2 |
| anion surfactant | 2 | 2 | 2 | 0.5 | 0.5 | 0.5 |
| benzo-isothiazolone | 0 | 0 | 0 | 0 | 0 | 0 |
| 2,2'-MBCP | 0 | 0 | 0 | 0 | 0 | 0 |
| cellulose ester | 0.1 | 0.3 | 0.5 | 0.1 | 0.3 | 0.3 |
| propyleneglycol | 10 | 10 | 10 | 10 | 10 | 10 |
| isopentane | 5 | 5 | 5 | 5 | 5 | 5 |
| water | 58 | 57.8 | 57.6 | 81.7 | 81.5 | 80 |
| viscosity(cP) | 6 | 12 | 292 | 6 | 12 | 12 |
| Aerosol traveling distance (cm) | 7 | 7 | 5 | 7 | 7 | 7 |
| Foam descending time (s/cm) | 6.3 | 71.7 | 276 | 6.3 | 71.7 | 71.7 |
| Foam falling time(s) | 730 | 940 | 3600 | 730 | 940 | 940 |
| Foam diminishing time(s) | 4200 | 7800 | 9780 | 4200 | 7800 | 7800 |
| Detergency | ○ | ○ | ○ | Δ | Δ | ○ |
| Anti-Legionella activity | ○ | ○ | ○ | ○ | ○ | ○ |
| General anti-bacterial activity | □ | □ | □ | □ | □ | □ |

TABLE 5

| ingredients | Exp. 16 | Exp. 17 | Exp. 18 |
|---|---|---|---|
| amine oxide | 0.7 | 0.7 | 0.7 |
| sodium metasilicate | 1.5 | 1.5 | 1.5 |
| aminoalcohol | 0 | 0 | 0 |
| nonion surfactant | 2 | 2 | 2 |
| anion surfactant | 0.5 | 0.5 | 0.5 |
| benzo-isothiazolone | 0.1 | 0.05 | 0.02 |
| 2,2'-MBCP | 0.1 | 0.05 | 0.02 |
| cellulose ester | 0.3 | 0.3 | 0.3 |
| propyleneglycol | 10 | 10 | 10 |
| isopentane | 5 | 5 | 5 |
| water | 79.8 | 79.9 | 79.96 |
| viscosity(cP) | 12 | 12 | 12 |
| Aerosol traveling distance (cm) | 7 | 7 | 7 |
| Foam descending time (s/cm) | 71.7 | 71.7 | 71.7 |
| Foam falling time(s) | 940 | 940 | 940 |
| Foam diminishing time(s) | 7800 | 7800 | 7800 |
| Detergency | ○ | ○ | ○ |
| Anti-Legionella activity | ○ | ○ | ○ |
| General anti-bacterial activity | ○ | ○ | ○ |

TABLE 6

| ingredient | Exp. 19 | Exp. 20 | Exp. 21 | Exp. 22 | Exp. 23 | Exp. 24 | Exp. 25 | Exp. 26 |
|---|---|---|---|---|---|---|---|---|
| amine oxide | 0.7 | 0.7 | 0.7 | 0.7 | 0.7 | 0.7 | 0.7 | 0.7 |
| sodium metasilicate | 0.1 | 0.5 | 5 | 15 | 1.5 | 1.5 | 1.5 | 1.5 |
| aminoalcohol | 0 | 0 | 0 | 0 | 0 | 0 | 0 | 0 |
| nonion surfactant | 4.2 | 4.2 | 4.2 | 4.2 | 0.01 | 0.1 | 10 | 15 |
| anion surfactant | 2 | 2 | 2 | 2 | 0.01 | 0.1 | 10 | 15 |
| benzoisothiazolone | 0.001 | 0.02 | 1 | 10 | 0 | 0 | 0 | 0 |
| 2,2'-MBCP | 0.001 | 0.02 | 1 | 10 | 0 | 0 | 0 | 0 |
| cellulose ester | 0.3 | 0.3 | 0.3 | 0.3 | 0.3 | 0.3 | 0.3 | 0.3 |
| propyleneglycol | 10 | 10 | 10 | 10 | 10 | 10 | 10 | 10 |
| isopentane | 5 | 5 | 5 | 5 | 5 | 5 | 5 | 5 |
| water | 77.698 | 77.26 | 70.8 | 42.8 | 82.48 | 82.3 | 62.5 | 52.5 |
| viscosity (cP) | 12 | 12 | 12 | 12 | 12 | 12 | 12 | 12 |
| Aerosol traveling distance (cm) | 7 | 7 | 7 | 7 | 7 | 7 | 7 | 7 |
| Foam descending time(s/cm) | 71.7 | 71.7 | 71.7 | 71.7 | 71.7 | 71.7 | 71.7 | 71.7 |
| Foam falling time(s) | 940 | 940 | 940 | 940 | 940 | 940 | 940 | 940 |
| Foam diminishing time(s) | 7800 | 7800 | 7800 | 7800 | 7800 | 7800 | 7800 | 7800 |
| Detergency | □ | ○ | ○ | ○ | □ | ○ | ○ | ○ |
| Anti-Legionella activity | ○ | ○ | ○ | ○ | ○ | ○ | ○ | ○ |
| General anti-bacterial activity | □ | ○ | ○ | ○ | □ | □ | □ | □ |

TABLE 7

| ingredients | Control 2 | Control 3 | Control 4 | Control 5 | Control 6 | Control 7 |
|---|---|---|---|---|---|---|
| amine oxide | 0.7 | 0.7 | 0 | 0 | 0.7 | 0 |
| sodium metasilicate | 1.5 | 1.5 | 1.5 | 1.5 | 1.5 | 0 |
| aminoalcohol | 20 | 20 | 20 | 20 | 0 | 20 |
| nonion surfactant | 4.2 | 4.2 | 4.2 | 4.2 | 0 | 4.2 |
| anion surfactant | 2 | 2 | 2 | 2 | 0 | 2 |
| benzo-isothiazolone | 0 | 0 | 0 | 0 | 0 | 0 |
| 2,2'-MBCP | 0 | 0 | 0 | 0 | 0 | 0 |
| cellulose ester | 0 | 0.1 | 0.1 | 0.3 | 0.3 | 0.3 |
| propyleneglycol | 10 | 10 | 10 | 10 | 10 | 10 |
| isopentane | 0 | 0 | 0 | 0 | 5 | 5 |
| water | 61.6 | 61.5 | 62.2 | 62 | 82.5 | 58.5 |
| viscosity(cP) | — | 6 | 6 | 12 | 12 | 12 |
| Aerosol traveling distance (cm) | 2.5 | 2.5 | 2.5 | 2.5 | 2.5 | 7 |
| Foam descending time (s/cm) | 0.7 | 2.7 | 2.7 | 5 | — | 71.7 |
| Foam falling time(s) | 8 | 96 | 96 | 120 | — | 940 |
| Foam diminishing time(s) | 139 | 3783 | 1800 | 2000 | — | 3900 |
| Detergency | x | □ | Δ | Δ | x | Δ |
| Anti-Legionella activity | Δ | Δ | Δ | Δ | Δ | x |
| General anti-bacterial activity | Δ | Δ | Δ | Δ | x | x |

Results

Greater aerosol traveling distance, foam descending time and foam falling time, as defined above, were observed for the mixture in experiment 7 than in control 2 and 3. It is obvious that the differences are attributable to the foaming agent and thickener added. The increase in these properties lead to longer contact time between microorganisms, or scale, onto which the cleaner is applied, and the cleaner. Consequently, the bactericidal effect and the cleaning effect are improved in experiment 7. The same improvements were observed with experiments 8 and 9.

The mixture in experiment 7 showed improved cleaning and anti-bacterial effect, when compared to control 4. The improvement in cleaning effect is believed to be caused by the extended foam falling time, which is defined above, due to the foaming agent added. General anti-bacterial activity was enhanced due to cooperation of sodium meta-silicate and amine oxides.

In experiments 10, 11, and 12, the aerosol traveling distance and foam falling time were improved, as in the cases of experiments 7,8, and 9. This led to an improved cleaning effect when compared to control 2. The cleaning effect was, however, not as great as that in experiments 7 to 9, since the mixture was free of sodium meta-silicate.

In experiments 13 and 14, improvements in the aerosol traveling time and foam falling time were also observed, as in the cases of experiments 7, 8, and 9. The cleaning effect of the mixtures were greater than that in control 2, but less than that in experiments 7 to 12 since the mixtures were free of sodium meta-silicate and amino alcohol.

Comparing experiment 15 with control 6, it turned out that the formation of foam was responsible for the improved cleaning and anti-bacterial effect, and that the presence of surfactants in the mixtures was essential for the foam to be formed. Considering the results of experiments 11,14, and 15, one effective way to enhance cleaning effect is to add sodium meta-silicate to the mixture. The comparison between experiment 8 and control 7 also implies the role of sodium meta-silicate in increasing the cleaning effect.

Comparing experiment 8 with control 7, it is concluded that the cleaning effect and the antimicrobial effect were improved in experiment 8. This indicates that the addition of sodium meta-silicate to the mixture improved the cleaning effect and improved the sanitizing effect of the mixture against bacteria in general, including Legionella.

As can be seen from the results of experiment 19 to 22, the amount of sodium meta-silicate in the mixture is preferably from 0.1 to 15% by weight. The amount of the second bactericide, benzoisothiazolone and/or benzalkonium, is preferably from 0.001 to 10% by weight. As shown in experiments 23 to 26, 0.1 to 15% by weight of anionic and non-ionic surfactants is preferably added to the mixture.

Anti-bacterial cleaning agents according to second embodiment of the present invention are suitable for sanitizing and cleaning aluminum fins, since they have grater anti-bacterial effect on a wide range of bacteria, including genus Legionella, and since they can penetrate into the narrow spaces between fins.

The cleaning agents according to the second embodiment of the present invention are especially preferred for cleaning and sanitizing aluminum fins since, after they have entered the narrow spaces between the fins, the cleaning agents adhere to the surfaces to be cleaned and sanitized, due to their viscosity.

Gaseous nitrogen was used as a propellant gas to spray the cleaning agents. Nitrogen is preferred for this purpose, since it neither reacts with the cleaning agents, nor dissolves in them.

Alternatively, the sixth embodiment may be modified as follows: the second bactericides may be dispensed with, in which case the bactericidal cleaning agents exhibit a cleaning effect as well as a selective anti-Legionella effect. Or, the cleaning agents may be free of pH regulators to ensure safe working conditions, since the pH values become substantially neutral without the pH regulators.

It should be apparent to those skilled in the art that the present invention may be embodied in many other specific forms without departing form the spirit or scope of the invention. Therefore, the present invention and embodiments are to be considered as illustrative and not restrictive, and the invention is not to be limited to the details given herein, but may be modified within the scope and equivalence of the appended claims.

What is claimed is:

1. A method for eradicating Legionella bacteria inhabiting in an air conditioning apparatus, comprising steps of:

obtaining an amine oxide bactericide solution consisting of at least one amine oxide represented by the formulae (1) or (2) as an active bactericide ingredient, an optional low boiling point compound, an optional pH regulator, an optional additional surfactant, and an optional thickener, the bactericide solution having an amine oxide concentration greater than or equal to 0.096 mM:

$$R_1\!-\!\!\!\underset{R_2}{\overset{R_2}{\underset{|}{N}}}\!\!\!\to O \qquad (1)$$

wherein $R_1$ represents $C_nH_{2n+1}(OC_2H_4)_m$, n varies from 12 to 18, m varies from 0 to 10, $R_2$ represents a hydrogen or alkyl group having from 1 to 4 carbon atom(s), and the solid arrow represents a coordinate bond between a nitrogen and oxygen;

$$R_1\!-\!\!\!\underset{R_3}{\overset{R_3}{\underset{|}{N}}}\!\!\!\to O \qquad (2)$$

wherein $R_1$ represents $C_nH_{2n+1}(OC_2H_4)_m$, n varies from 12 to 18, m varies from 0 to 10, $R_3$ represents $(C_pH_{2p})OH$ with p varying from 1 to 4, and the solid arrow represents a coordinate bond between a nitrogen and oxygen, and wherein 0.42 mM of the bactericide solution eradicates $10^8$ CFU/ml of the Legionella bacteria when the bactericide solution contacts the Legionella bacteria for fifteen minutes; and applying the amine oxide bactericide solution to a surface of the air conditioning apparatus occupied by Legionella bacteria so that the bactericide solution remains in contact with the bacteria to eradicate the bacteria.

2. A method for eradicating Legionella bacteria according to claim 1, wherein the amine oxide solution remains in contact with the Legionella bacteria for at least three hours.

3. A method for eradicating Legionella bacteria according to claim 1, wherein the amine oxide solution is canned with propellant gas and capable of being sprayed on the surface.

4. A method for eradicating Legionella bacteria according to claim 3, wherein the propellant gas is compressed gaseous nitrogen.

5. A method for eradicating Legionella bacteria according to claim 3, wherein the low boiling point compound has a boiling point between 10° C. and 40° C. to generate foam after spraying the amine oxide solution on the surface.

6. A method for eradicating Legionella bacteria according to claim 5, wherein the low-boiling foaming compound comprises an amount about 5% by weight of the amine oxide solution.

7. A method for eradicating Legionella bacteria according to claim 1, wherein the amine oxide concentration is less than or equal to 50 mM.

8. A method for eradicating Legionella bacteria according to claim 1, wherein the pH regulator regulates the pH value of the solution.

9. A method for eradicating Legionella bacteria according to claim 1, wherein the pH regulator is a basic agent.

10. A method for eradicating Legionella bacteria according to claim 9, wherein the basic agent is sodium metasilicate.

11. A method for eradicating Legionella bacteria according to claim 1, wherein the additional surfactant is an anionic-type surfactant.

12. A method for eradicating Legionella bacteria according to claim 11, wherein the additional surfactant has a concentration in the amine oxide solution from 0.01 to 15% by weight.

13. A method for eradicating Legionella bacteria according to claim 11, wherein the additional surfactant has a concentration in the amine oxide solution from 0.1 to 10% by weight.

14. A method for eradicating Legionella bacteria according to claim 1, wherein the additional surfactant is non-ionic-type surfactant.

15. A method for eradicating Legionella bacteria according to claim 14, wherein the additional surfactant has a concentration in the amine oxide solution from 0.01 to 15% by weight.

16. A method for eradicating Legionella bacteria according to claim 14, wherein the additional surfactant has a concentration in the amine oxide solution from 0.1 to 10% by weight.

17. A method for eradicating Legionella bacteria according to claim 1, wherein the thickener is a material selected from the group consisting of sodium alginate, propylene glycol alginate esters, carboxymethyl cellulose (CMC) esters, sodium carboxymethyl cellulose, starch sodium glycolate, starch sodium phosphate esters, methyl cellulose, sodium polyacrylate, cellulose esters, alginic acid, casein, and poly-N-vinyl acetamide.

18. A method for eradicating Legionella bacteria according to claim 1, wherein the amount of amine oxide in the amine oxide solution is from 0.007 to 7% by weight.

19. A method for eradicating Legionella bacteria according to claim 1, wherein the surface includes a surface of a fin heat exchanger of the air conditioning apparatus.

20. A method for eradicating Legionella bacteria on heat exchange fins of an air conditioning appar wherein $R_1$ represents $C_nH_{2n+1}(OC_2H_4)_m$, n varies from 12 to 18, m varies from 0 to 10, $R_2$ represents a hydrogen or alkyl group having from 1 to 4 carbon atom(s), and the solid arrow represents a coordinate bond between a nitrogen and oxygen;

$$R_1-\underset{R_3}{\overset{R_3}{N}}\to O \qquad (2)$$

wherein $R_1$ represents $C_nH_{2n+1}(OC_2H_4)_m$, n varies from 12 to 18, m varies from 0 to 10, $R_3$ represents $(C_pH_{2p})OH$ with p varying from 1 to 4, and the solid arrow represents a coordinate bond between a nitrogen and oxygen; and applying the amine oxide bactericide solution to a surface of the air conditioning apparatus occupied by Legionella bacteria so that the bactericide solution remains in contact with the bactericide to eradicate the bacteria.

* * * * *